United States Patent [19]

Koll

[11] Patent Number: 4,653,510

[45] Date of Patent: * Mar. 31, 1987

[54] APPARATUS FOR COLLECTING AND/OR GROWING PROTECTED BIOLOGICAL CULTURES

[75] Inventor: Laurel A. Koll, Ruleville, Miss.

[73] Assignee: Accu-Med Corporation, Ruleville, Miss.

[*] Notice: The portion of the term of this patent subsequent to Dec. 4, 2001 has been disclaimed.

[21] Appl. No.: 677,732

[22] Filed: Dec. 3, 1984

Related U.S. Application Data

[63] Continuation-in-part of Ser. No. 333,220, Mar. 1, 1982, Pat. No. 4,485,824.

[51] Int. Cl.$^4$ .............................................. A61B 10/00
[52] U.S. Cl. .................................... 128/756; 128/759; 435/295; 435/296; 604/1
[58] Field of Search ........................ 128/749, 756–759; 604/1, 221, 222; 435/295, 296, 810

[56] References Cited

U.S. PATENT DOCUMENTS

| | | | |
|---|---|---|---|
| 3,212,685 | 10/1965 | Swan et al. | 604/222 |
| 3,857,384 | 12/1974 | Watson | 128/749 |
| 4,030,498 | 6/1977 | Tompkins | 604/222 |
| 4,467,816 | 8/1984 | Schlüter | 128/756 |
| 4,485,824 | 12/1984 | Koll | 128/756 |

Primary Examiner—Edward M. Coven
Assistant Examiner—John C. Hanley
Attorney, Agent, or Firm—Nixon & Vanderhye

[57] ABSTRACT

The coaxial annular space between a rod and a slidably received outer cylinder is divided into three serial chambers by four seals. Two seals are spaced apart and affixed to the front of the rod. Two seals are spaced apart and affixed to the cylinder rearwardly of the first two. By relative forward rod movement, a specimen capturing zone is exposed at the desired site of a biological specimen. Thereafter, rearward rod movement re-seals the capturing zone. Further, rearward rod movement reduces the volume of a media containing chamber and thereby moves the collection zone into contact with the desired medium. The third chamber prevents contamination of the biologically active portions of the structure during operation. Pre-scored break lines formed in the cylinder and rod facilitate severance of unneeded portions after collection of a biological specimen and/or after transportation to a suitable laboratory facility. Color-coded indicia are used on the rod and/or cylinder so as to facilitate proper operation. Reusable extension pieces may be attached to the cylinder and/or rod so as to adapt a standard size module to different desired end uses.

32 Claims, 8 Drawing Figures

APPARATUS FOR COLLECTING AND/OR GROWING PROTECTED BIOLOGICAL CULTURES

This application is a continuation-in-part of my copending application Ser. No. 353,220 filed Mar. 1, 1982 now U.S. Pat. No. 4,485,824 and allowed on June 25, 1984. The entire disclosure of this parent application is hereby expressly incorporated by reference.

This invention is also generally directed to apparatus for collecting, transporting and/or growing protected biological specimens. It is particularly directed to a novel structure for obtaining, transporting and/or growing biological specimens which are completely protected from contamination at all times after initial capture.

As explained in my earlier filed parent application, the problem of protecting a biological specimen from contamination during and after its initial capture is an old one. That is, it is well known that unless special precautions are taken, a given biological specimen may inadvertently become contaminated during the collection process and/or during transfer of the collected specimen to a growing medium or the like. Once thus contaminated, the worth of this specimen for diagnostic or research purposes may be greatly reduced or even eliminated.

Since specimens are obtained in non-sterile environments for the most part, it is imperative that the specimen be protected from contamination by passage through the outer extremities of body cavities from which they have been collected as well as from ambient air which, for example, also generally contains bacteria. For successful capture of any anerobic bacteria, one simply must protect it from contact with the air. Any contamination with bacteria from ambient air or the outer extremities of body cavities or the like often provides false or misleading diagnosis of the condition sought.

Many prior approaches to this problem are discussed in the specification of my earlier-filed parent application and in the USPTO prosecution history of that application. However, none of these prior approaches are believed to provide method or structure as advantageous as that disclosed and claimed in my earlier patent application and/or as disclosed and claimed in the present application.

The exemplary embodiment disclosed in my earlier parent application utilized a flexible "front" and "middle" seal spaced apart from one another, attached toward one end of a rod and slidably received within a coaxial tube assembly. An absorbent specimen capturing structure was typically attached behind the front seal and a biological growth medium or other desired transport or protective medium was then disposed in a variable volume chamber defined behind the "middle" seal and in front of a "rear" seal attached to the other end of the outer coaxial tube (and through which the rod was slideably disposed). Thus, forward relative motion of the rod exposed the capturing structure at the desired biological site while subsequent rearward movement of the rod resealed the end of the assembly and, if continued, reduced the volume of the media containing chamber so as to place the collected biological specimen into contact with the desired medium (earlier contained solely within this variable volume chamber). The portion of the rod which was caused to enter into a biologically active area of the device during forward motion of the rod was protected from contamination by a thin stripable elastomer coating or the like. The outer cylinder was also disclosed as possibly being pre-scored along preferred break lines so as to facilitate severance of unneeded excess portions of the structure after the biological specimen had been captured and moved into contact with the desired medium.

Since the filing of my earlier parent application, I have discovered a new and presently preferred exemplary embodiment which is, in some respects, improved over the embodiment disclosed in my earlier application.

For example, I now dispose the "rear" seal within the tube and relatively closer to the "middle" rod seal. I have also added a spaced-apart "barrier" seal similar to the "rear" seal but disposed rearwardly thereof so as to protect the length of rod which enters into the biologically active portions of the device upon forward motion of the rod to capture a biological specimen. In effect, the new type of "barrier" seal disposed rearward of the "rear" seal takes the place of the earlier utilized stripable elastomeric film which was used as a form of "barrier" seal in my earlier exemplary embodiment.

By moving the "rear" seal forwardly inside the tube and by using a spaced apart "barrier" seal to the rear thereof, the overall device has enhanced versatility as well as possibly lower manufacturing costs and more convenience in use.

For example, where the "rear" seal is actually placed at the rear end of the tube, the variable volume media-containing chamber defined between that and the middle seal on the rod is typically much larger than required for containing the desired quantity of medium (e.g. where usage in some deep body cavity is contemplated and therefore a substantial length of tubing is contemplated). When this situation occurs, it necessarily implies that the biological growth medium (or other desired protective medium contained within this variable volume chamber) is exposed to a relatively large internal surface area of the outer cylinder structure. When the cylinder is made of plastic material, for example, it may have a substantial water absorption rate. Under these circumstances, when the desired biological medium has a water base (as is typically the case), any gas in the device would soon become saturated with water from the desired medium and the plastic material will then begin to absorb such water at its natural water absorption rate. If the absorption rate of the material is relatively high, then the desired water content of the biological medium within the variable volume chamber will change and the whole device may be rendered unusable after some given period of time.

However, by moving the "rear" seal inside and forwardly of the tube, the nominal storage volume of the medium-containing chamber defined between the rear seal and the "middle seal" may be reduced to a more optimum size while simultaneously reducing its exposure to water absorbing surface area and thereby extending the useful shelf life of the product.

Furthermore, by placing both the "rear" and the "barrier" seals internally of the cylinder, much greater design freedom is provided so as to facilitate the adaptation of the device to particular applications. For example, by using a barrier seal spaced rearwardly of the rear seal (by a distance that is at least equal to the maximum required forward movement of the inner rod during specimen capture procedures), one still provides an effective sterile barrier for the inner rod (i.e. portions of the rod exposed to unsterile conditions never pass into the biologically active chambers containing either the specimen or the biological growth/protective medium) but one avoids the necessity for providing a dip coat seal or "balloon" type seal as proposed in my earlier exemplary embodiment. In addition, by disposing the desired biological medium nearer the front of the tube, the overall length of the device can be substantially shortened with related savings in manufacturing costs, transportation, handling, etc. Indeed, a fairly short standarized size may be thus adapted, with the use of reuseable extensions (if desired), to facilitate useage of the standard size device in deep body cavities (or for any other desired application where longer instrument length is needed or desired).

On the other hand, if reusable extension portions are not desired for some reason, then one may still obtain advantages as noted above by placing the "rear" seal closer to the front of the tube so as to reduce the nominal volume of the medium-containing chamber. Here, if desired, the barrier seal may be placed near or at the rear portion of the desired longer length tube, all of which would then be simply broken off and discarded after the desired specimen has been captured.

I have also discovered an improved placement of simple grooves or score lines at various predetermined places on the cylinder and/or rod so as to facilitate the severance of these elements at predetermined locations at various times in the planned useage of the device. For example, a doctor or veterinarian might typically break off the outer cylinder and inner rod at first predetermined places after a specimen has been successfully captured and properly located in the desired biological medium within the outer tube. If desired, these predetermined locations might be color coded (e.g. with a blue colorant). Subsequently, after the thus shortened device has been transported to a proper laboratory environment, it may be further shortened by severance at an additional predetermined point (e.g. also color coded with a red colorant) so as to permit convenient laboratory access to the specimen under controlled environmental conditions.

Additional color-coded indicia or the like are also preferably employed along the moveable rod so as to provide markers facilitating the proper magnitude of forward and rearward motions of the rod (e.g. during the specimen capturing procedure and/or during subsequent rearward movement of the rod so as to place this captured specimen into contact with the desired biological medium).

These as well as other objects and advantages of this invention will be better understood by reading the following detailed description of the presently preferred exemplary embodiment of this invention taken in conjunction with the accompanying drawings, of which:

Figure 1:
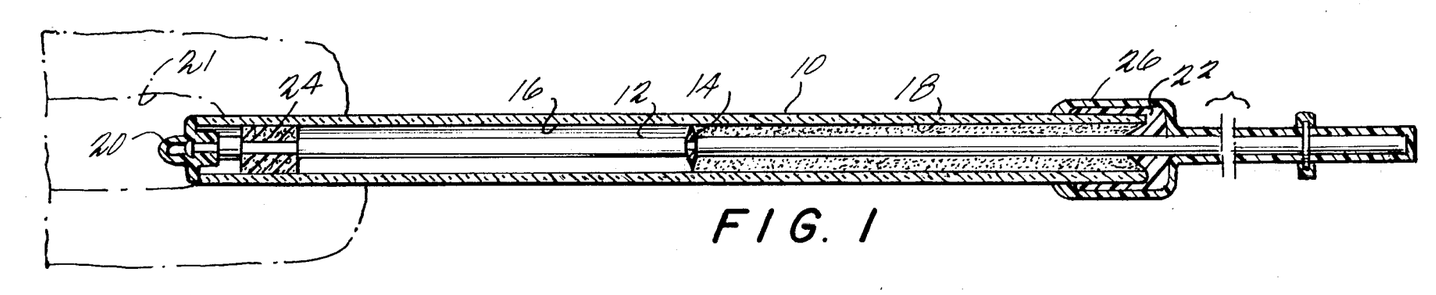
FIG. 1 is a cross-sectional view of the earlier preferred exemplary embodiment described more fully in my above-referenced parent application.

My earlier preferred exemplary embodiment is depicted at FIG. 1 and is described more completely in my earlier-referenced parent application. As shown, it includes an elongated outer protective cylinder 10 and an inner rod 12 having an even greater length. Typically the rod and cylinder are made of transparent glass or plastic or the like. For purposes of illustration, the rightmost ends of the cylinder and rod assembly (which assembly might also be thought of as a piston 12 and cylinder 10 assembly or simply as coaxial means) will be referred to as the "rear" ends while the left-most ends as shown in FIG. 1 will be referred to as the "forward" ends. The same relative orientation will be used throughout this application for describing relative locations along the rod and/or cylinder structures.

As may be observed in FIG. 1, the outside diameter of rod 12 is materially less than the inside diameter of the cylinder 10. There is therefore a coaxial space created between the rod and cylinder in which various materials may be contained. This coaxial space is subdivided by various seals into a series of chambers. For example, a specimen capturing zone or chamber 16 is defined between a flexible "front" seal 20 affixed to the front end of rod 12 and a flexible "middle" seal 14 also affixed to rod 12 but at a position spaced rearwardly of the "front" seal 20. This specimen collection zone 16 typically includes an absorbent specimen collection structure 24 attached to rod 12. Before use, chamber 16 is sealed from outside contaminants by front seal 20.

A second chamber 18 is also defined between "middle" seal 14 and a "rear" seal 22 which is fixably attached to cylinder 10 rearwardly of the middle seal 14. Chamber 18 is typically initially filled with a culture growth medium, a culture transport medium, a biological release agent or the like. As shown in FIG. 1 by stippling, this filling may, for example, normally fill substantially all of chamber 18. The remainder of chamber 18 and of chamber 16 normally may be filled with a non-contaminated, non-reactive gas or liquid.

After the distal end of the entire structure is inserted to a desired site of a biological specimen (e.g. deep within an internal organ 21 of a human or animal), the rod 12 is moved forwardly so as to expose the collection zone 16 and the absorbent structure 24 to the desired biological specimen. It should be observed that by moving rod 12 forwardly, the volume of cavity 18 has been increased while cavity 16 has been unsealed so as to permit capture of the desired biological specimen. The disk-like middle seal 14 has a flexible periphery that may be chosen to have a desired degree of stiffness by choosing its thickness, material, etc. as will be appreciated. In some embodiments, it may be desirable to make the periphery of the disk-like middle seal 14 quite flexible such that part of the inert filling from chamber 16 will actually flex the periphery of the middle seal 14 and pass into chamber 18 when the rod is moved forwardly thus relieving a relatively lower pressure in chamber 18 caused by forward movement of rod 12. On the other hand, in other embodiments, it may be desired to make the disk-like seal somewhat stiffer in its periphery so as to leave a relatively lower pressure in chamber 18 as the rod 12 is moved forwardly. In this latter instance, when the rod 12 is again moved rearwardly so as to compress the contents of chamber 18, a relatively lower pressure area may be created in chamber 16 so as to draw additional volumes of biological specimen into that chamber.

Typically, when the instrument has rod 12 moved forwardly so as to capture a biological specimen, the operator will be holding the rear end of the assembly and thereby be able to move the distal end of the extended and opened assembly within the internal organ so as to ensure absorption of the desired biological specimen (within the structure 24, for example). Thereafter, rod 12 is moved rearwardly and the front cap-like seal 20 inverts so as to provide sliding and sealing contact with the inside walls of the cylinder 10.

The volume of chamber 18 is necessarily reduced by continued rearward movement of rod 12 (e.g. after removal from the body organ). This produces a pressure buildup of the desired biological medium in chamber 18 until the periphery of the disk-like middle seal is flexed to permit the pre-filled material in chamber 18 to pass into contact with the captured biological specimen in the chamber 16. As should be appreciated, any excess material in the now shrinking combined volume of chambers 18 and 16 is also permitted to pass outwardly past the inverted cap-like front seal 20.

In this manner, a desired biological specimen may be captured at its natural site and transferred to a desired growth medium or the like within the coaxial sealed chambers 16 and 18.

The only conceivable source of contamination might be via the rearward normally extended surface of rod 12. If this surface should become contaminated, then it is conceivable that some contamination might pass rear seal 22 and into the biologically active chamber 18 as the rod is moved forwardly.

In the embodiment of FIG. 1, such possible contamination is prevented by a thin protective outer or "barrier" seal 26. This thin outer seal 26 may be provided, for example, in the form of a dip coating of a medical grade elastomer to a point past the forward end of the rear seal 22. This thin layer of an elastomer or the like may then be simply be stripped from the rod by the Chevron-type rear seal as the rod is moved forwardly into the outer tube so as to "pile up" against the rear seal during forward rod movement. During subsequent rearward rod movement, the thin flexible seal 26 may break or otherwise loose its sealing properties. However, such would be of no consequence since the inside pressure of the assembly is then above the ambient thus preventing inward passage of materials past seals and the like. Furthermore, there is no further contemplated forward movement of the rod after the barrier seal 26 might be broken.

The presently preferred and improved exemplary embodiment is depicted at FIGS. 2-8. To facilitate understanding, structures having similar functions in this new preferred embodiment are identified by the same reference numerals used for corresponding portions of the FIG. 1 embodiment. Thus, there is still an inner rod 12 slidably contained within a larger coaxial tube 10. A flexible "front" seal 20 and "middle" seal 14 are fixed toward the forward end of rod 12 so as to define a specimen capturing zone or chamber 16 therebetween. An absorbent specimen collection structure 24 is typically disposed about the rod 12 within this area between front seal 20 and middle seal 14.

Figure 2:
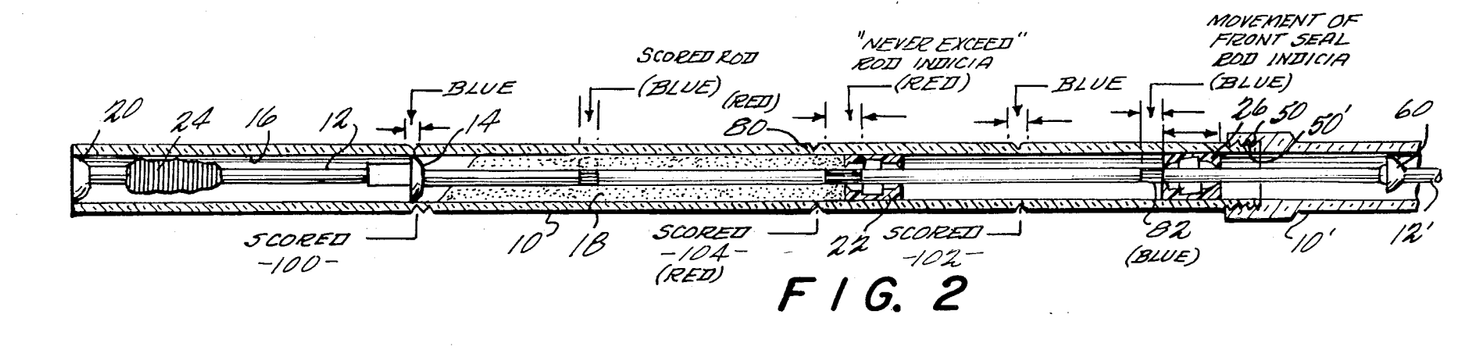
FIG. 2 is a cross-sectional view of the presently preferred exemplary embodiment of my invention in its initial assembled and filled condition prior to actual usage.

Rear seal 22 has now been moved inside and forwardly of cylinder 10. However, it still defines a second medium-containing chamber 18 between it and the middle seal 14. Barrier seal 26 is, in this embodiment, now constructed to be identical to the rear seal 22 and is spaced rearwardly thereof by a distance that is at least equal to the expected forward travel of rod 12 during the specimen capturing procedure. In this manner, the limited section of rod 12 which moves forwardly through rear seal 22 into the biologically active zone 18 is protected by a third chamber between seals 22 and 26.

Since chambers 16 and 18 can now both be disposed toward the front end of cylinder 10 in standardized positions, the biologically active portions of the device may be made in a standard-sized module 50. For some applications, this may be of a suitable size for end usage. For other applications (e.g. for equine uterine culture collections), a considerably longer structure may be physically required for access to the desired biological site. If so, then a reusable (or disposable) cylinder extension 10' and/or a resuable (or disposable) rod extension 12' may be operatively attached to cylinder 10 and rod 12 respectively.

For example, as depicted in FIG. 2, the rear end of cylinder 10 may include a threaded portion 50 which mates with a threaded portion 50' of a cylinder extension 10' of suitable length. Similarly, a ball and socket type coupling 60 or the like may be utilized to connect the ends of rod 12 and the rod extension 12' as also depicted in FIG. 2. Other types of conventional mechanical couplings may also be utilized for such connections of the extension 10' and 12' as should be appreciated.

The operation of the active standard-sized module 50 is similar to that of my earlier preferred embodiment depicted in FIG. 1. In brief, the assembly is supplied to a user in the condition depicted at FIG. 2 with chamber 18 having a desired medium therewithin and with chamber 16 being sealed by the forward seal 20. After placement of the front end of the module 50 at a desired biological site, then rod 12 is moved forwardly with respect to cylinder 10 so as to expose the collection zone 16 and the absorbent structure 24. After a desired specimen is therein captured, and before the device is removed from the desired site, rod 12 is then moved rearwardly within cylinder 10 to at least reseal the forward end of the tube with forward seal 20 before it is withdrawn from the biological site. Thereafter, if desired, the rod 12 may be further drawn rearwardly so as to move the just captured specimen on structure 24 into contact with the desired medium initially contained within chamber 18. Of course, as rod 12 is moved to the rear, the volume of chamber 18 ever diminishes thus forcing the medium material contained therewithin to pass by the middle seal 14 and into contact with the captured specimen. Ultimately, the volume of chamber 18 is decreased to a very small or even zero volume and one is left with the device in the condition shown at FIG. 3. Pre scored break points 100, 102 on cylinder 10 and breakpoint 102' on rod 12 may then be utilized by the doctor or veterinarian or other operating personnel so as to conveniently sever the now unneeded end portions of the rod and cylinder assembly. This greatly facilitates collection of the biologically active portions of the device that need to be transported to the laboratory or other environment for further processing and/or analysis.

Figure 3:
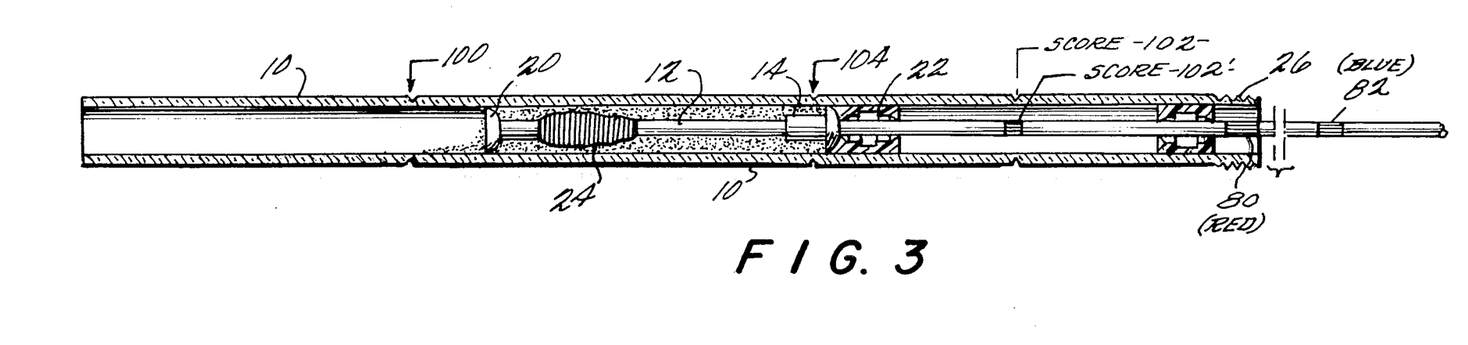
FIG. 3 is a cross-sectional view like that of FIG. 2 but showing the inner rod in a rearwardly retracted position so as to place a captured specimen into contact with the desired biological medium.

Once the biologically active portions of the module arrive at the laboratory, then a further break point 104 may be utilized by the laboratory technican so as to break away more of the outer tube 10 and again provide access to rod 12 for conveniently withdrawing the biological culture from the tube assembly. Of course, as will be appreciated, such access to the collected biological specimen would be carried out only under controlled laboratory conditions suitable for the type of bacteria or the like that is being collected.

In the preferred exemplary embodiment, the initial break points 100, 102 and 102' (e.g. for use by the doctor or veterinarian) are color coded with a blue colorant. The break point 104 intended for usage only under controlled laboratory conditions is preferably marked with a red colorant indicating to the initial user that it is not yet to be utilized.

In addition, in the preferred exemplary embodiment, additional operator guidance indicia are provided on the rod at points 80 and 82. For example, in the quiescent initial condition depicted in FIG. 2, these marks may be substantially coincident with the rear ends of seals 22 and 26 respectively. The desired degree of forward motion may then be gauged by the operator by observing indicia 82 through transparent tube 10 as the rod 12 is moved forwardly. Care should be taken so as to never move the indicia 82 beyond the rear seal 22. On the other hand, indicia 80 provides an important piece of operator information when the rod 12 is moved rearwardly since, when indicia 80 is aligned at the rearend of barrier seal 26, this may be dimensioned so as to indicate a "never exceed" mark where the middle seal 14 is already in position near the rear seal 22 and further rearward movement of the rod 12 should not be attempted. Of course, this might also be indicated by alignment of the color-coded break points 102' and 102 which should also occur when the indicia 80 is properly positioned with respect to barrier seal 26 as also indicated in FIG. 3. In the preferred exemplary embodiment, the forward movement limit indicia 82 is marked by a blue colorant while the rearward rod movement limit indicia 80 is marked with a red colorant. It should be appreciated that such forward and rearward "movement limits indicia" might be otherwise disposed on the rod and/or cylinder so as to depict the desired degree of relative motions.

Figure 4:
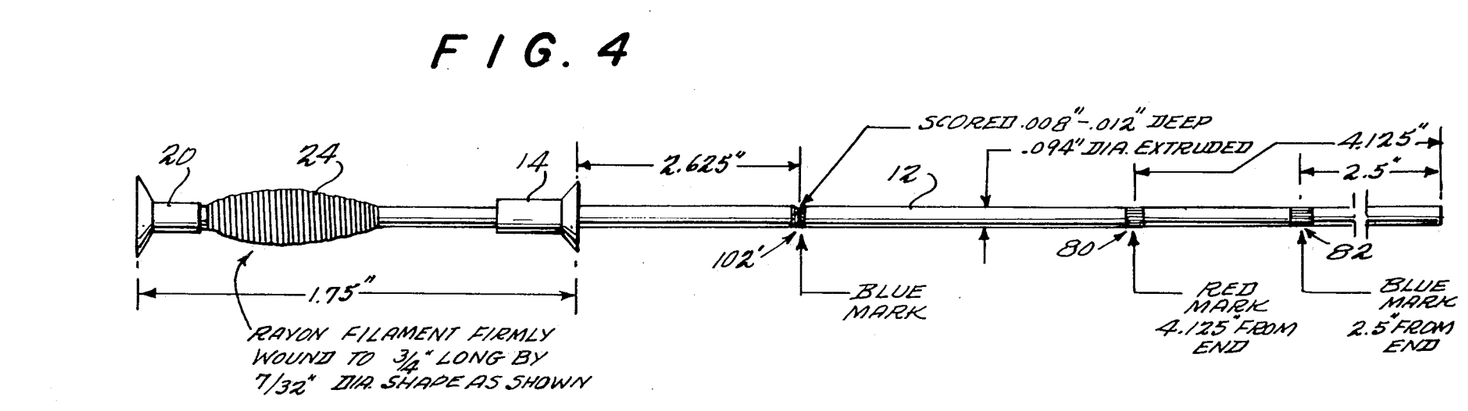
FIG. 4 is a side view of the rod subassembly used in the exemplary embodiment of FIGS. 2 and 3.
Figure 5:
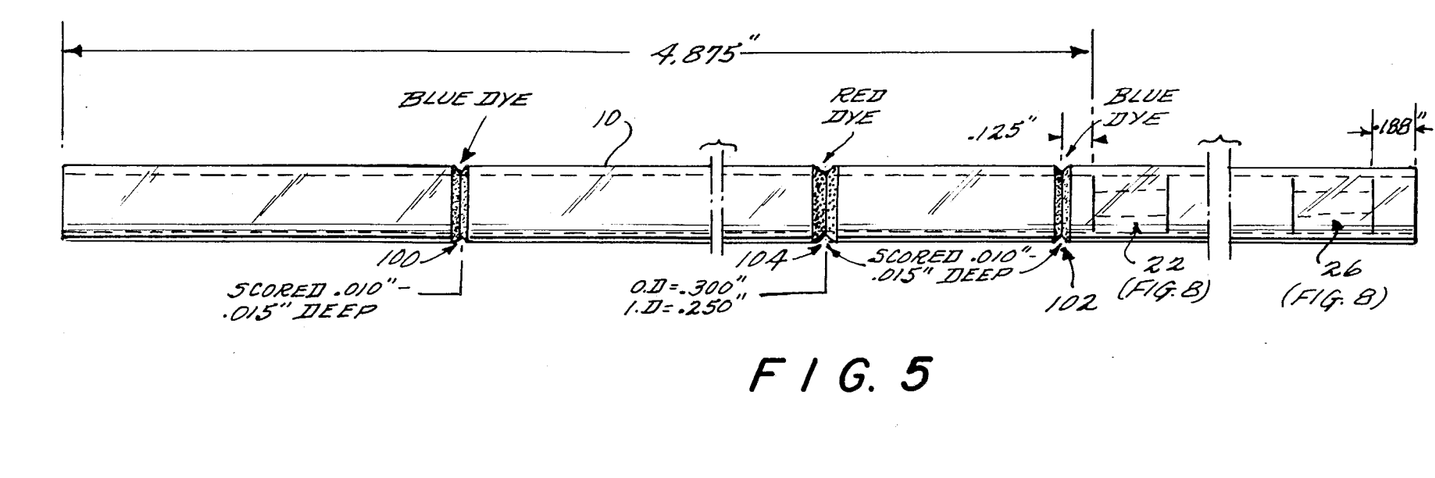
FIG. 5 is a side view of the tube subassembly utilized in the exemplary embodiment of FIGS. 2 and 3.

The rod subassembly is depicted in FIG. 4 while the cylinder subassembly is depicted at FIG. 5. In the preferred exemplary embodiment, the rod subassembly of FIG. 4 is assembled with the cylinder by inserting it into the front end of cylinder 5 with a rearward and twisting motion through the center sealing bores of seals 22 and 26. When the middle seal 14 is approximately ¼ inch or so from the front end of tube 10, an approximately 1/16 inch outside diameter media filler tube is inserted into the tube 10 so as to insert the desired quantity of media (e.g. 1 cubic centimeter) into chamber 18. Before removing the media filler tube, the rod 12 may be further slid rearwardly to its desired quiescent position. It is preferrable to avoid any forward motion of rod 12 during this procedure so that the lips of both the front seal 20 and the middle seal 14 are pointed forwardly as depicted in FIG. 3. Thereafter, the medium filler tube may be withdrawn past the front seal 20. This method of assemblage will ensure ambient pressure in the medium chamber 18.

Although the rod 12 and tube 10 may be made from many suitable medical grade materials, in the preferred exemplary embodiment, they are preferably formed by an extruded plastic of the types typically used for medical applications. A polypropolyene or polyester type of plastic may be used. At least the outer tube 10 is preferrably transparent so as to facilitate its operation in the manner described.

The seals may also be made from many different materials. However, in the preferred exemplary embodiment, they are molded from thermoplastic rubber, or other similar materials. A thermosetting silicone rubber may be used. In one exemplary embodiment, the flexible seals have a hardness of approximately 35–40 durometer.

In the present exemplary embodiment, the seals may be secured to their respective structures (e.g. the outside diameter of rod 12 or the inside diameter of tube 10) by suitable friction fits. For example, the molded inside diameter of the seals 20 and 14 may be made less than the outside diameter rod 12 such that when they are stretched and placed into position on the rod, there is a significant friction force maintaining them in the desired positions. On the other hand, seals 22 and 26 may have an outside diameter somewhat larger than the inside diameter of tube 10. If so, when they are compressed and forceably positioned (e.g. with a punch type mechanism) into place within tube 10, there is a substantial frictional force present to also secure them at the desired relative locations. (At the same time, the center passage holes in seals 22 and 26 for rod 12 must also be suitably sized so as to provide a slideable but sealed condition). One exemplary set of dimensions for providing such friction fits is depicted in the drawings.

Figure 6:
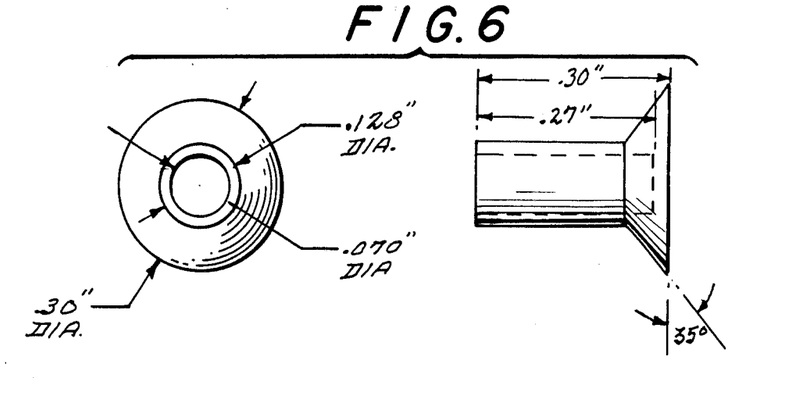
FIG. 6 is a side and end view of the flexible "front" seal used in the exemplary embodiment of FIGS. 2 and 3.
Figure 7:
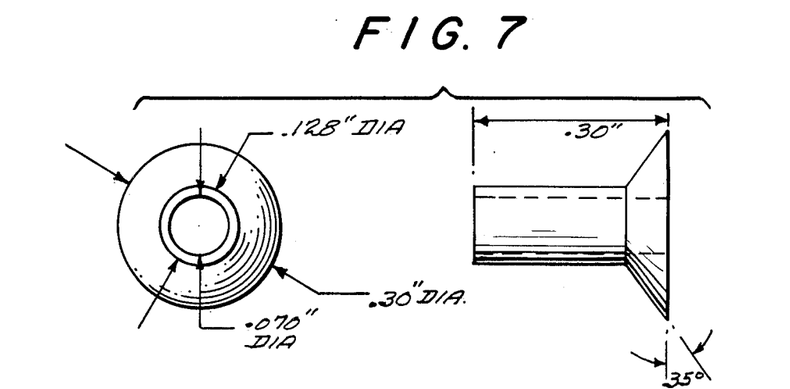
FIG. 7 is a side and end view of the flexible "middle" seal utilized in the exemplary embodiment of FIGS. 2 and 3.
Figure 8:
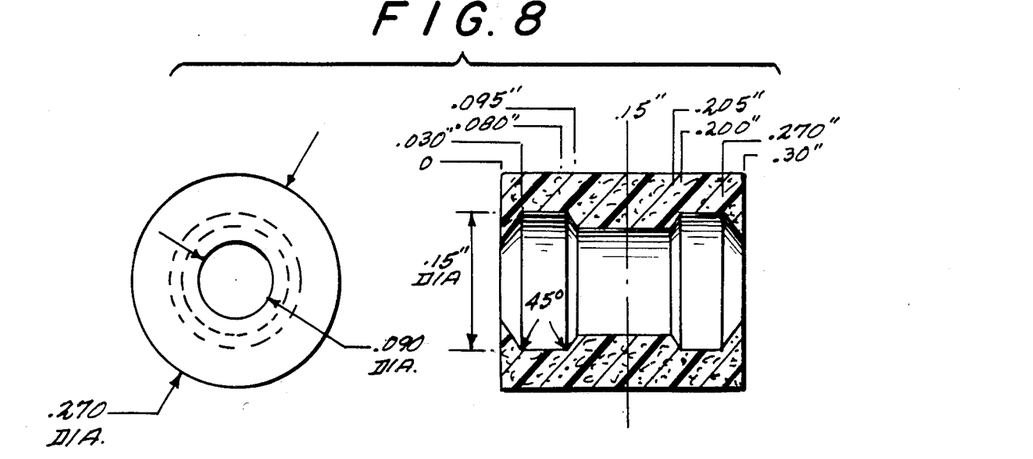
FIG. 8 is a side and end view of the "rear" and/or "barrier" seal utilized in the exemplary embodiment of FIGS. 2 and 3.

In one exemplary embodiment, a silicone rubber (e.g. Silastic Q7) may be molded to the exemplary dismensions shown in FIGS. 6–8 to form seals 14, 20, 22 and 26 for use with the exemplary dimensions of the cylinder and rod as depicted in FIGS. 4 and 5. However, it should be understood that these specific dimensions are only exemplary and that many other dimensions and materials and forms of construction may be utilized to realize the structure of this invention. For example, instead of a friction fit to secure the seals to the desired respective rod and cylinder locations, suitable adhesives or other securement mechanisms may be utilized as should be appreciated.

As should now be appreciated, the improved embodiment of FIGS. 2–8 provides a structure wherein the medium-containing chamber 18 may be minimized in size so as to minimize the problems caused by water absorption into the walls of the plastic or other material used to define that chamber. At the same time, this new structure facilitates the realization of a standard sized module 50. If longer devices are desired for particular applications, then disposable or reusable extensions may be connected to the operative portions of the structure.

Particularly advantageous pre-scored break points are also provided for use immediately after specimen collection and/or after transportation to a controlled laboratory environment so as to facilitate the overall usage of the device. These pre-scored break lines may be conveniently color coded so as to help ensure that they are properly used by the proper personnel during the entire intend life usage of a particular apparatus.

In addition, operational indicia (preferrably color coded) are provided on the slidable rod so as to indicate the preferred extends of maximum forward and rearward movement with respect to the initial nominal starting position as supplied to the end user.

In the preferred exemplary embodiment, blue color coding is used to indicate the break points for a doctor or veterinarian to use while a red colored break point is used so as to caution the doctor or veterinarian not to break the tube at that point. However, if the doctor or other initial user of the device properly breaks it off at the blue break points, then when it arrives at a controlled laboratory environment, the remaining red marked break point indicates where the laboratory technician should further break the structure.

In the preferred exemplary embodiment, a blue mark signifying a rearward stopping place is applied to the rod so as to indicate where the rod movement should be stopped prior to withdrawal of the unit from the cavity (i.e. when the front seal 20 is in place and sealing the collection zone 16). Once removed from the cavity, then rod 12 may be further pulled rearwardly—but a red "not to exceed" mark is preferably placed at an appropriate point on the rod so as to signify the maximum permitted rearward movement without damage to the device and/or protected specimen that has just been collected.

The scored break point on the rod is also preferably blue colored and is moved into alignment with a blue colored break point on the external cylinder after the rod is withdrawn to its rear most position where the swab 24 is immersed in the desired medium such that both the inner rod and the outer tubing can be conveniently snapped off substantially simultaneously at these aligned points.

The use of color coding or the various indicia and break off points substantially enhances the ease with which this device may be successfully utilized in the field. While the colors red and blue are preferred, it should be understood that other color combinations might prove just as appropriate and/or useful. Furthermore, there may be more than two colors used in some color coding schemes as will be appreciated. It is also possible to include additional indicia as may be desired in the future (e.g. an orange "caution" marking might be utilized just prior to the red "never exceed" marking on the rod 12). It should be noted that since the various scorings and markings are measured from the ends of the tubing and rod and related to inter-seal spacings, the same sort of arrangement may be utilized with much longer assemblies.

As an example of one typical set of instructions for usage of this device by a doctor or veterinarian and subsequently by a laboratory technician, the following is provided:

EXEMPLARY DIRECTIONS FOR USE BY DOCTOR OR VETERINARIAN

1. Remove entire device 50 from its sleeve package and insert the forward end of the device into body cavity to the desired depth, BY PUSHING ON THE OUTER TUBE ONLY. Use speculum when applicable.
2. HOLD REARWARD portion of OUTER TUBE while grasping REARWARD END of INNER ROD with thumb and forefinger. Push INNER ROD FORWARD until fingers contact tube, and pull REARWARD approximately ONE AND ONE HALF INCHES (1½"). NEVER PULL the INNER ROD REARWARD enough to allow the BLUE LINE on the REARWARD portion of the INNER ROD, to EXTEND PAST the REARWARD END of OUTER TUBE. Repeat several times to assure saturation of the swab.
3. BEFORE WITHDRAWING FROM CAVITY, PULL INNER ROD BACK until the BLUE LINE is near the REARWARD END of the OUTER TUBE. (This will assure that the SPECIMEN IS COMPLETELY SEALED before withdrawal). Remove the entire device 50 from the cavity by PULLING ON THE OUTER TUBE ONLY.
4. Elevate the FORWARD end of device 50 by 45 degrees. While holding the OUTER TUBE, SLOWLY PULL INNER ROD REARWARD (to place swab in transport medium) until REAR SLIDING SEAL (DIRECTLY BEHIND SWAB) is TOUCHING STOP at REARWARD END of MEDIUM, (OPPOSITE RED SCORE MARK ON OUTER TUBE) and/or RED MARK on REARWARD portion of INNER ROD is even with REARWARD END of OUTER TUBE. CAUTION . . . NEVER PULL RED MARK ON INNER ROD PAST END OF OUTER TUBE!
5. CAUTION: NEVER PUSH INNER ROD FORWARD AFTER COLLECTING SPECIMEN.
6. BREAK OUTER TUBE at BOTH BLUE SCORED RINGS by placing BOTH THUMBS TOGETHER AT EACH BLUE RING and SNAPPING the tubing off WITH SHARP, 90 DEGREE MOTION. BE CAREFUL NOT TO BREAK TUBING AT THE RED CENTER SCORED RING. THE SMALL INNER ROD WILL BREAK, AT ITS BLUE MARK, AS THE REAR BLUE SCORED RING BREAKS.
7. Place the shortened device 50 in a transport tube (forward end first) and CAP TIGHTLY.
8. Complete specimen identification and transport it to laboratory without delay.

EXEMPLARY INSTRUCTIONS FOR USE BY LABORATORY TECHNICIAN

1. OPEN IN ANAEROBIC ENVIRONMENT.
2. REMOVE device FROM OUTER PROTECTIVE CONTAINER.
3. Place BOTH THUMBS against RED SCORED RING ON TUBING and GENTLY APPLY PRESSURE to BREAK TUBING. ROTATE TUBING, IF NECESSARY, TO BREAK OPPOSITE SIDE, SO AS NOT TO BEND INNER ROD EXCESSIVELY. Pull FORWARD END OF TUBING (longest part of tubing) FORWARD to remove, exposing the swab.
4. BEFORE STREAKING DISH, CUT OFF SMALL FORWARD SEAL (rubber flange just ahead of swab) WITH HEAT STERILIZED INSTRUMENT (SCISSORS, SCALPEL, ETC.). DO NOT USE ALCOHOL DISINFECTED INSTRUMENTS.
5. HOLDING SMALL REMAINING PORTION OF OUTER TUBE, STREAK ANAEROBIC AND AEROBIC CULTURE DISHES with swab.
6. Properly dispose of remaining device parts.

While only one presently preferred exemplary embodiment has been described in detail, those skilled in the art will recognize that many modifications and variations may be made in this exemplary embodiment while still retaining many of the advantageous novel features of this invention. Accordingly, all such modifications and variations are intended to be included within the scope of the following claims.

What is claimed is:

1. Apparatus for collecting a biological specimen, said apparatus comprising:
   first and second coaxially disposed cylindrical structures;
   first and second spaced-apart flexible seal means being secured to said first coaxial structure and slidably received within said second coaxial structure to define a biological specimen collection cavity therebetween; biological specimen collection means disposed in said cavity,
   third and fourth spaced-apart seal means being secured to said second coaxial structure and slidably receiving said first coaxial structure therewithin to define two additional chambers within said second coaxial structure, and
   said third and fourth seal means being spaced apart by a predetermined distance.

2. Apparatus as in claim 1 wherein said first and second coaxial structures include color-coded pre-scored break-points to facilitate severance of unneeded portions after collection of a biological specimen.

3. Apparatus as in claim 1 wherein at least one of said coaxial structures includes indicia means indicating predetermined limits of relative sliding motions thereof in first and second directions.

4. Apparatus as in claim 1 wherein one end of said first and second coaxial structures include connection means for connecting another structure thereto and further comprising:
   first and second extension means respectively connectable to said connection means of the first and second coaxial structures so as to extend the effective structural length thereof.

5. Apparatus for collecting a biological specimen, said apparatus comprising:
   first and second elongated structures slidably connected with one another and including means for defining a series of sealed chambers therebetween;
   a biological specimen collection means being disposed in a first one of said chambers and being placeable into contact with a biological specimen site by relative motion of said first and second elongated structures in a first direction;
   a predetermined biological medium being disposed in a second one of said chamber which includes means for placing said medium into contact with a collected biological specimen in said first chamber by relative motion of said first and second elongated structures in a second direction;
   said first and second elongated structures including color-coded pre-scored breakpoints to facilitate severance of unneeded portions after collection of a biological specimen; and
   at least one of said first and second elongated structures also including color-coded indicia means indicating predetermined limits of distance of relative motions thereof in said first and second directions.

6. Apparatus for collecting a biological specimen, said apparatus comprising:
   a hollow first structure having a front end and a rear end and an internal passage therethrough from said front end to said rear end;
   an elongated second structure slidably disposed within said internal passage and also having a front end and a rear end;
   a flexible front seal secured to said second structure at a predetermined location and slidable within said passage;
   a flexible middle seal secured to said second structure at a point rearward of said front seal and also slidable within said passage;
   a rear seal secured to said first structure and disposed within said passage at a point rearward of said middle seal and through which said second structure is slidably disposed;
   a cavity having a variable volume defined by the hollow first structure, the elongated second structure, the middle seal, and the rear seal;
   a barrier seal secured to said first structure at a point rearward of said rear seal and through which said second structure is slidably disposed; and
   specimen collection means disposed on said second structure at a collection point located rearward of said front seal and forward of said middle seal, said zone thus being slidable with said second structure with respect to said first structure such that (a) by relative forward movement of the second structure, said front seal and at least part of said zone is extended beyond the forward end of the first structure and into an exposed position for contacting a biological specimen and (b) by subsequent relative rearward movement of the second structure, said front seal is moved rearwardly within said passage.

7. Apparatus as in claim 6 further comprising a biological medium material disposed in said cavity having variable volume, the volume of said cavity being decreased as said rearward motion is effected whereby said collection means is moved into the presence of said medium material as that collection means is moved rearwardly.

8. Apparatus as in claim 6 wherein said barrier seal is spaced from said rear seal by a distance at least equal to the distance of said forward movement.

9. Apparatus as in claim 6 wherein said front and middle seals are each secured to said second structure by a friction fit therabout.

10. Apparatus as in claim 6 wherein said rear and barrier seals are each secured to said first structure by a friction fit within said internal passageway.

11. Apparatus as in claim 6 further comprising:
    a first extension connection structure disposed at the rear end of said first structure;
    a second extension connection structure disposed at the rear end of said second structure.

12. Apparatus as in claim 11 further comprising:
    a first elongated extension member connectable via said first extension connection structure with said first structure; and
    a second elongated extension member connectable via said second extension connection structure with said second structure.

13. Apparatus as in claim 6 wherein
    said hollow first structure includes walls having break means formed therein at least one predetermined location for facilitating the severance of an unneeded portion therefrom after a specimen has been captured in said zone.

14. Apparatus as in claim 13 wherein said walls include two break means, each being disposed a respective predetermined distance from a respectively associated end of the first structure for facilitating the severance of unneeded portions from each end thereof after a specimen has been captured.

15. Apparatus as in claim 14 wherein said walls further include a third break means disposed between the other two break means at a predetermined location to facilitate the severance of a further unneeded portion of the first structure after transportation of a captured specimen therein to a laboratory environment.

16. Apparatus as in claim 13, 14 or 15 wherein said second structure also includes a break means for facilitating the severance of an unneeded portion therefrom after a specimen has been captured in said zone.

17. Apparatus as in claim 16 wherein said break means on the second structure is disposed in approximate alignment with a break means on the first structure when said middle seal is moved rearwardly to the vicinity of said rear seal so that unneeded portions of both said first and second structures can be severed substantially simultaneously.

18. Apparatus as in claim 12, 14 or 15 wherein at least some of said break means are color-coded with a distinctive colorant.

19. Apparatus as in claim 15 wherein two of said break means are associated with a first distinctive colorant and another break means disposed therebetween is associated with a second distinctive colorant.

20. Apparatus as in claim 6 wherein said second structure bears spaced-apart visible indicia means located to guide the user in determining the proper extent of said forward and said rearward movement.

21. Apparatus for collecting a biological specimen, said apparatus comprising:
a cylinder having a front end and a rear end and an internal passage therethrough from said front end to said rear end;
a rod slidably disposed within said internal passage and also having a front end and a rear end;
a flexible front seal secured to said rod at its front end and slidable within said passage;
a flexible middle seal secured to said rod at a point rearward of said front seal and also slidable within said
a rear seal secured to the internal passage of said cylinder at a point rearward of said middle seal and through which said rod is slidably disposed;
a cavity having a variable volume defined by the cylinder, the rod, the middle seal, and the rear seal;
a barrier seal secured to said cylinder at a point rearward of said rear seal and through which said rod is slidably disposed; and
a specimen collection means disposed on said rod in a space located rearward of said front seal and forward of said middle seal, said collection means thus being slidable with said rod with respect to said cylinder such that, by a predetermined distance of forward movement of the rod relative to the cylinder, said front seal and part of said collection means may be extended beyond the forward end of the cylinder and into position for contacting the site of a desired biological specimen when disposed at such a site.

22. Apparatus as in claim 21 further comprising a biological growth material means disposed in said cavity, said variable volume of the cavity being decreased as said rod is moved rearwardly whereby said growth material means is caused to deflect and pass around the flexible middle seal and into the specimen collection means as that means moves rearwardly.

23. Apparatus as in claim 21 wherein said barrier seal is spaced rearwardly of said rear seal by a predetermined distance at least equal to said predetermined distance of said forward movement.

24. Apparatus as in claim 21 wherein said barrier seal is secured to the inside of said cylinder.

25. Apparatus as in claim 21 wherein said front seal is secured to said rod by a friction fit thereabout.

26. Apparatus as in claim 21 wherein said middle seal is secured to said rod by a friction fit thereabout.

27. Apparatus as in claim 21 wherein said rear seal is secured to said cylinder by a friction fit therewithin.

28. Apparatus as in claim 21 wherein said barrier seal is secured to said cylinder by a friction fit within said passage.

29. Apparatus as in claim 21, 22 or 23 wherein:

said front and middle seals are each secured to said rod by a friction fit thereabout; and said rear and barrier seals are each secured to said cylinder by a friction fit within said passage.

said rear and barrier seals are each secured to said cylinder by a friction fit within said passage.

30. Apparatus as in claim 21 wherein:

said rear ends of the cylinder and of the rod each include an extension connection means for connecting respectively associated elongated extension members thereto.

31. Apparatus as in claim 30 further comprising:

a first elongated extension member means adapted to be removably connected to the rear end of said cylinder;

a second elongated extension member means adapted to be removably connected to the rear end of said rod.

32. Apparatus as in claim 31 wherein the connection means on said cylinder and first extension member means comprises mating threaded structures and wherein the connection means on said rod and said second extension member means comprises a mated ball and socket structure.

* * * * *